(12) United States Patent  
Babiner

(10) Patent No.: US 9,339,357 B1
(45) Date of Patent: *May 17, 2016

(54) MULTI-HEADED TOOTHBRUSH

(71) Applicant: Maxim Babiner, Philadelphia, PA (US)

(72) Inventor: Maxim Babiner, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,664

(22) Filed: Feb. 9, 2015

Related U.S. Application Data

(60) Provisional application No. 61/965,882, filed on Feb. 7, 2014.

(51) Int. Cl.
    *A61C 17/34* (2006.01)
    *A46B 5/00* (2006.01)
    *A46B 9/04* (2006.01)
    *A61C 17/22* (2006.01)

(52) U.S. Cl.
    CPC ............... *A61C 17/349* (2013.01); *A46B 9/045* (2013.01); *A61C 17/222* (2013.01)

(58) Field of Classification Search
    CPC ..... A61C 17/349; A61C 17/222; A46B 9/045
    See application file for complete search history.

(56) References Cited

U.S. PATENT DOCUMENTS

| | | | |
|---|---|---|---|
| 5,305,491 A | 4/1994 | Hegemann | |
| 5,407,254 A | 4/1995 | Hegemann | |
| 5,471,702 A | 12/1995 | Schmitt | |
| 5,499,421 A | 3/1996 | Brice | |
| D374,351 S | 10/1996 | Van Kempen | |
| 5,673,454 A | 10/1997 | Quintanilla et al. | |
| 5,749,380 A | 5/1998 | Zebuhr | |
| 5,749,381 A | 5/1998 | Butler et al. | |
| 5,758,380 A | 6/1998 | Vrignaud | |
| 5,934,762 A | 8/1999 | Vrignaud | |
| 6,108,852 A | 8/2000 | Vrignaud | |
| 6,112,361 A | 9/2000 | Brice | |
| 6,199,821 B1 | 3/2001 | Job | |
| 6,209,164 B1 | 4/2001 | Sato | |
| 6,334,232 B1 | 1/2002 | Sato | |
| 6,381,794 B1 | 5/2002 | Porper et al. | |
| 6,823,554 B1 | 11/2004 | Braun et al. | |
| 7,059,853 B2 | 6/2006 | Hegemann | |
| 7,363,823 B2 | 4/2008 | Brice | |
| 7,757,328 B2 | 7/2010 | Hegemann et al. | |
| 7,757,329 B2 | 7/2010 | Hegemann | |
| 7,757,330 B2 * | 7/2010 | Hegemann ........... | A61C 1/0092 15/22.1 |
| 7,805,796 B2 | 10/2010 | Winter et al. | |
| 7,849,549 B2 | 12/2010 | Hegemann et al. | |
| 8,245,348 B2 | 8/2012 | Winter et al. | |
| 8,449,295 B2 | 5/2013 | Hegemann | |
| 8,505,148 B2 | 8/2013 | Atkin | |
| 8,997,298 B2 * | 4/2015 | Krasnick .............. | A46B 5/0066 15/159.1 |
| 2007/0169295 A1 | 7/2007 | Winter et al. | |
| 2011/0067191 A1 | 3/2011 | Atkin | |
| 2012/0279002 A1 | 11/2012 | Sokol et al. | |

FOREIGN PATENT DOCUMENTS

| | | |
|---|---|---|
| DE | 102012021262 A1 | 5/2013 |
| GB | 2404849 A | 2/2005 |

(Continued)

*Primary Examiner* — Shay Karls

(74) *Attorney, Agent, or Firm* — James M. Smedley LLC; James Michael Smedley, Esq.

(57) ABSTRACT

The present invention generally relates to oral hygiene. In particular, embodiments of the invention relate to a multi-headed toothbrush and method for brushing teeth.

15 Claims, 4 Drawing Sheets

(56) References Cited

FOREIGN PATENT DOCUMENTS

| | | |
|---|---|---|
| GB | 2404849 B | 5/2006 |
| KR | 200453026 Y1 | 3/2011 |
| WO | WO2005087134 A1 | 9/2005 |
| WO | WO2009137671 A1 | 11/2009 |
| WO | WO2012151259 A1 | 11/2012 |

* cited by examiner

MULTI-HEADED TOOTHBRUSH

CROSS-REFERENCE TO RELATED APPLICATIONS

This application claims the benefit of U.S. Provisional Application 61/965,882 entitled Multi-Headed Toothbrush, filed Feb. 7, 2014, the entire contents of which are incorporated herein by reference in its entirety for all purposes.

BACKGROUND OF THE INVENTION

The present invention generally relates to oral hygiene. In particular, embodiments of the invention relate to a multi-headed toothbrush and method for brushing teeth.

A known apparatus to brush teeth with multiple brush heads described in U.S. Pat. No. 5,673,454A involves the use of a three-headed brush that enables the user to accomplish brushing of all exposed sides of the user's teeth simultaneously. Disadvantageously, the rigid nature of such multi-headed brushes as the type disclosed in U.S. Pat. No. 5,673,454A, do not conform to tooth and gum structures of different anatomical sizes and qualities, causing suboptimal pressure on teeth and gums.

Inventions in the prior art include a variety of improvements to the basic toothbrush such as a three-headed brush that touches three tooth faces simultaneously (U.S. Pat. No. 5,673,454A) to shorten the necessary brushing time by 3 times. Additionally, the invention disclosed in US 20120279002 A1, is a toothbrush that incorporates sonic oscillation technology to aid in the removal of plaque without a back and forth motion. No inventions in the prior art eliminate the problems of pinching the bodies of the mouth and gums while enabling the transmittal of sonic energy motion to a multi-headed toothbrush.

SUMMARY OF THE INVENTION

It has been left for the present inventor to discover a solution to the problem of pinching that is typically associated with three headed toothbrushes. It has also been left for the present inventor to discover a solution to the challenge of transmission of sonic energy through flexible materials included in a brush head.

At the heart of the present invention is a toothbrush with three heads that are able to be connected to a handle in such a way that they have the ability to flex independently of one another. This toothbrush also allows for the transfer of energy associated with sonic motion or other motion to the brush heads. In this way, vibration or other motion generated by a mechanism located the handle of the brush can be transferred to the brush head, reducing the amount of work that the user has to perform to clean his or her teeth. The invention still retains the benefits of multi-headed toothbrushing by allowing for teeth to be cleaned in a fraction of the time required to clean teeth while utilizing traditional single brush head methods, while avoiding the requirement for a user to perform a back and forth motion user dexterity and the pinching of mouth bodies typically associated with multi-headed toothbrushes.

In a preferred embodiment of the invention, the three brush heads form a single unit, each connected to one another through flexible attachment arms. In such embodiment, the three heads independently flex when pressure is applied to the teeth for a consistent pressure on each tooth independent of the shape of the tooth. For instance, in this preferred embodiment of the invention, consistent pressure is applied regardless of whether the tooth is a narrow tooth such as an incisor, or a wide tooth such as a molar.

In embodiments of the invention, the multi-headed brush head unit is able to connect to a variety of toothbrush handles that are known in the prior art as well as other items that could act as a toothbrush handle. In a preferred embodiment of the invention, sonic motion is generated with a motor in the handle and this motion transmits to the brush heads through independently flexing attachment structures. A preferred embodiment of the invention specifically uses DuPont bristles.

DETAILED DESCRIPTION OF CERTAIN EMBODIMENTS OF THE INVENTION

Figure 1:
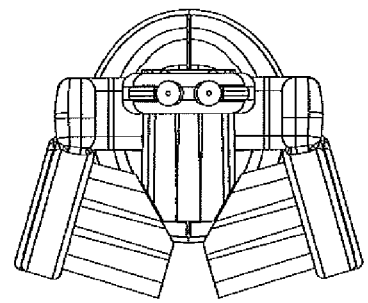
FIG. 1 Top-down view of the preferred embodiment of the invention.
Figure 2:
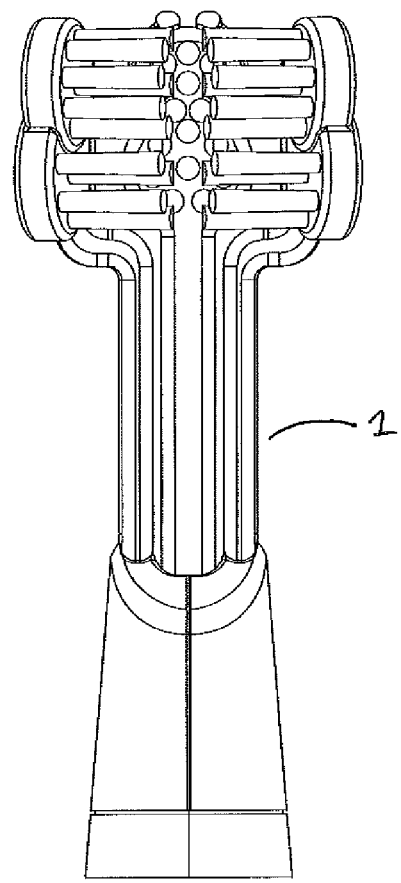
FIG. 2 Frontal view of the preferred embodiment of the invention.

The tooth brushing devices known in the prior art comprise a handle attached directly to a brush head. The handle is used to control the motion of the brush head. The brush head is used to directly dislodge plaque and debris from the teeth, gums, and other mouth structures. The simple versions of toothbrushes known in the prior art have a single head attached to a stiff, solid handle.

The handles of toothbrushes in the prior art are simple and made of plastic, wood, or other stiff material. The handle can be narrow, molded, simple, or complexly shaped. Alternatively, toothbrushes have a flexible neck region between the stiff handle and the brush head. Additional modifications include a motorized handle that provides a spinning action or sonic action to the bristles.

In the prior art, the bristles in a toothbrush head are arranged in various conformations. The simplest embodiment is a series of bristle clusters in a grid formation of three by ten. The bristle clusters can be variable in density and arrangement.

Toothbrush bristles are either made of hard rubber or a toothbrush bristle material made exclusively by DuPont. The preferred embodiment of the present invention uses the DuPont bristles.

The common tendency for users to brush for 45 seconds instead of the 2 minute duration recommended by the American Dental Association results in teeth that are not sufficiently cleaned using a simple, single-head toothbrush. One improvement over the single-head toothbrush, and one that addresses this problem directly, is a three-headed toothbrush. A three-headed toothbrush (as in U.S. Pat. No. 5,673,454A) cuts the time of brushing by three because three faces of the teeth are brushed simultaneously. A three-headed toothbrush also solves the problem of focusing inadequate time on the palatal side of the tooth as people tend to focus on the buccal side instead. The three headed toothbrush forces a user to brush the lingual, buccal, and bite sides of the teeth equally.

Three headed toothbrushes need to apply pressure to the teeth as they brush, so that the bristles can remove material from multiple directions simultaneously. However, three-headed toothbrushes with stiff necks, such as that disclosed by U.S. Pat. No. 5,673,454A, are known to cause pinching of the gums and teeth, which can be painful or even damaging to mouth structures. The preferred embodiment of the present invention solves that problem via three-headed toothbrush containing a flexible neck region that attaches each head to the handle independently preventing excessive pressure and pinching.

A simple toothbrush relies on the user to provide a physical back-and-forth action that requires skill and deft motor function of the arm and hands. A problem, therefore, that accompanies many tooth-brushing activities, is that children, the elderly, the disabled, and others who suffer limitations in motor function are limited in their ability to adequately clean their teeth with traditional tooth-brushing motions. The preferred embodiment of the present invention solves that problem by incorporating into its design a toothbrush with bristles that vibrate, spin, or provide sonic motion overcomes the need for the user to have dexterous control of the toothbrush.

Figure 5:
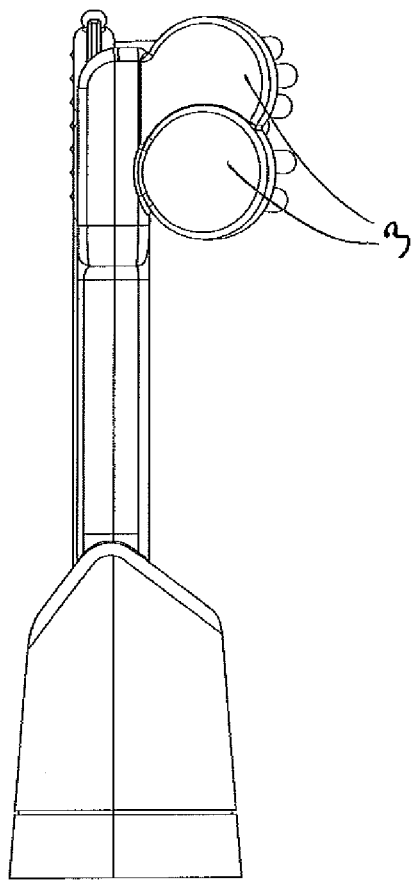
FIG. 5 View from left side of the preferred embodiment of the invention.
Figure 6:
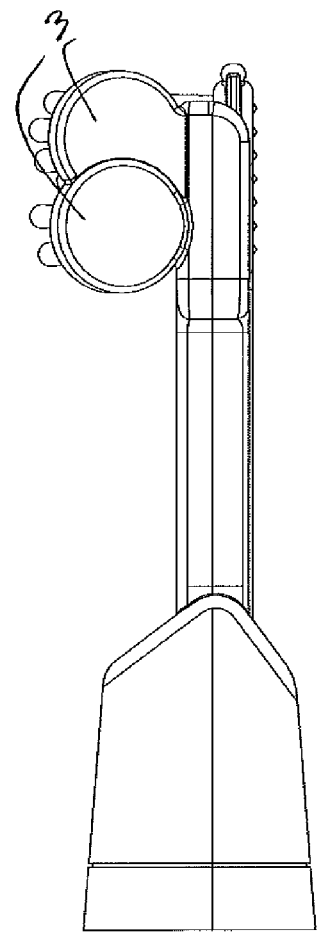
FIG. 6 View from right side of the preferred embodiment of the invention.
Figure 7:
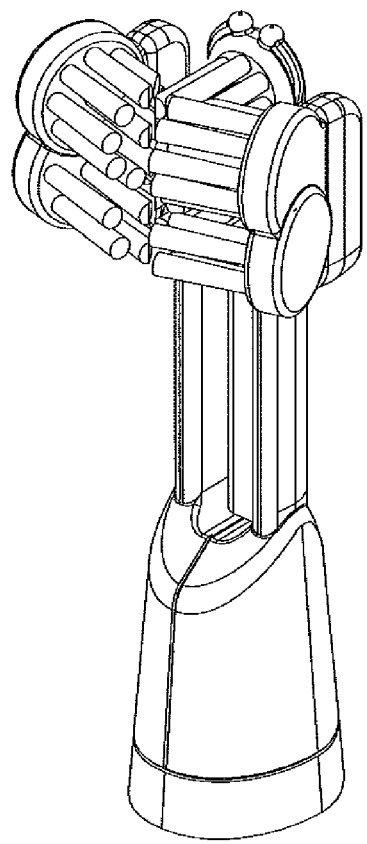
FIG. 7 Top angular view of a preferred embodiment of the invention.

As noted above, it remained for the present inventor to recognize that a combination of toothbrush improvements have never been present in the same device. Embodiments of the present invention incorporate the benefits of a three-headed toothbrush, flexible neck regions 1, and the capability to deliver sonic action through the bristles. The present inventor has discovered that the flexible neck region available in prior art prevented the transmission of sonic motion to the bristles. Embodiments of the present invention incorporate a rigid brush head material, such as plastic, in such a manner that allows the brush neck to flex with the contours of bodies of the mouth while still transmitting the energy necessary to facilitate the sonic motions of the brush. FIG. 5 and FIG. 6 disclose rounded heads 3 that incorporate means to transmit sonic or spinning energy to the bristles of the brush.

Figure 3:
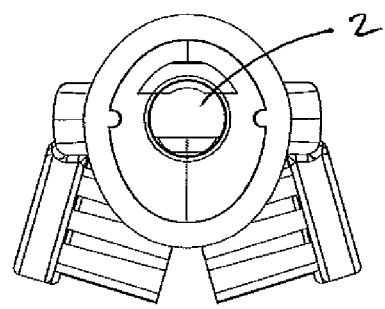
FIG. 3 Bottom-up view of the preferred embodiment of the invention.
Figure 4:
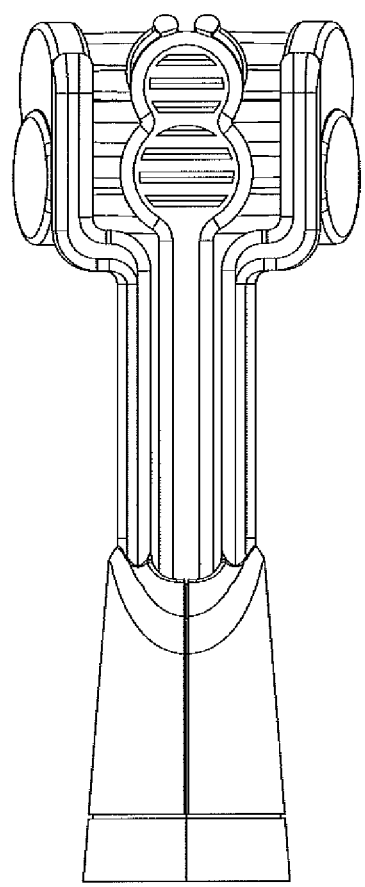
FIG. 4 Rear view of the preferred embodiment of the invention.

Embodiments of the present invention comprise only of a head and neck region that is removable from the handle. This allows for an economical change to a fresh toothbrush head when the bristles become worn. FIG. 3 discloses a cavity 2 incorporated into one embodiment of the invention showing a means to securely attach the embodiment of the invention to a brush head handle. Similarly, the head and neck unit of an embodiment of the present invention can be made to fit onto multiple types of handles.

A toothbrush embodying the principles of the invention can include a variety of bristle conformations. Such bristles can be long or short; they can be a uniform length, or variable in length. The inventor has noted that short bristles are effectively stiffer and the length of bristles can be used to vary the stiffness while using the same materials. In embodiments of the invention, bristles can be very dense or sparsely placed. In embodiments of the invention, each of the three heads can mirror the others in bristle length and conformation or the conformation can be different between heads.

What is claimed is:

1. A toothbrush comprising:
a first component comprising a first neck and a first head having first bristles;
a second component comprising a second neck and a second head having second bristles;
a third component comprising a third neck and a third head having third bristles; and
a handle coupled to the first component, the second component, and the third component,
wherein each of the first neck, the second neck and the third neck flexes independently of each other, and wherein the handle generates and transmits energy to at least one of the first, second, and third bristles.

2. The toothbrush of claim 1, wherein a first distance between the first bristles and the second bristles and a second distance between the second bristles and the third bristles allow vibration for cleaning.

3. The toothbrush of claim 2, wherein the first distance and the second distance are two millimeters.

4. The toothbrush of claim 1, wherein the first, second, and third components comprise acrylonitrile butadiene styrene.

5. The toothbrush of claim 1, wherein the handle is removably coupled to the first base, the second base, and the third base.

6. The toothbrush of claim 1, wherein the first, second, and third bristles have a diameter of 0.127 millimeters.

7. The toothbrush of claim 1, wherein the energy causes movement of the bristles.

8. The toothbrush of claim 7, wherein the movement comprises at least one of vibration, spinning and sonic oscillation.

9. A bristle assembly comprising:
a first component comprising a a first neck and a first head having first bristles;
a second component comprising a a second neck and a second head having second bristles; and
a third component comprising a third neck and a third head having third bristles, wherein
each of the first neck, the second neck, and the third neck flexes independently of each other, and
the first component, the second component, and the third component are coupled together so as to form a cavity configured to receive a handle.

10. The bristle assembly of claim 9, wherein the first, second, and third components transmit energy received from the handle to the first, second, and third bristles, respectively.

11. The bristle assembly of claim 10, wherein a first distance between the first bristles and the second bristles and a second distance between the second bristles and the third bristles allow vibration for cleaning.

12. The toothbrush of claim 10, wherein the first distance and the second distance are two millimeters.

13. The bristle assembly of claim 10, wherein the energy causes movement of the bristles.

14. The bristle assembly of claim 13, wherein the movement comprises at least one of vibration, spinning and sonic oscillation.

15. The bristle assembly of claim 9, wherein the first, second, and third components comprise acrylonitrile butadiene styrene.

* * * * *